United States Patent [19]
Calello et al.

[11] Patent Number: 6,080,390
[45] Date of Patent: Jun. 27, 2000

[54] MOISTURIZING COSMETIC STICK COMPOSITIONS

[75] Inventors: Joseph Frank Calello, Union; Janet Elizabeth Opel, Brick; Renee Joan Ordino, Edison; Robert Walter Sandewicz, Spotswood, all of N.J.; Natividad R. Jose, Jamaica, N.Y.

[73] Assignee: Revlon Consumer Products Corporation, New York, N.Y.

[21] Appl. No.: 09/435,847

[22] Filed: Nov. 8, 1999

Related U.S. Application Data

[63] Continuation of application No. 08/918,134, Aug. 27, 1997.

[51] Int. Cl.$^7$ .......................... A61K 7/027; A61K 7/032
[52] U.S. Cl. ........................... 424/64; 424/63; 424/401; 424/DIG. 5; 424/195.1
[58] Field of Search .................... 424/63, 64, DIG. 5, 424/401, 195.1

[56] References Cited

U.S. PATENT DOCUMENTS

| | | | |
|---|---|---|---|
| 4,137,302 | 1/1979 | Humbert | 424/47 |
| 4,246,257 | 1/1981 | Elliott | 424/78 |
| 4,336,246 | 6/1982 | Leon-Pekarek | 424/70 |
| 4,370,319 | 1/1983 | Chapio | 424/184 |
| 4,424,234 | 1/1984 | Alderson | 424/317 |
| 4,508,703 | 4/1985 | Redziniak | 424/38 |
| 4,515,784 | 5/1985 | Bogardus | 514/63 |
| 4,650,670 | 3/1987 | Callingham | 424/65 |
| 4,661,343 | 4/1987 | Zabotto | 424/59 |
| 4,678,663 | 7/1987 | Scott | 424/62 |
| 4,797,273 | 1/1989 | Linn | 424/59 |
| 4,816,261 | 3/1989 | Luebbe | 424/65 |
| 4,826,828 | 5/1989 | Wilmott | 514/63 |
| 4,879,114 | 11/1989 | Catsimpoolas | 424/95 |
| 4,888,363 | 12/1989 | Dulak | 514/725 |
| 4,911,925 | 3/1990 | Shatkina | 424/401 |
| 4,950,688 | 8/1990 | Bowsen | 514/847 |
| 5,000,945 | 3/1991 | Kobayashi | 424/59 |
| 5,084,427 | 1/1992 | Tsoulcalas | 502/62 |
| 5,085,855 | 2/1992 | Shore | 424/64 |
| 5,085,856 | 2/1992 | Dunphy | 424/64 |
| 5,091,171 | 2/1992 | Yu | 424/642 |
| 5,098,712 | 3/1992 | Ohno | 424/401 |
| 5,114,717 | 5/1992 | Kuznitz | 424/401 |
| 5,118,507 | 6/1992 | Clement | 424/401 |
| 5,124,081 | 6/1992 | Vanlerberghe | 424/450 |
| 5,128,123 | 7/1992 | Brewster | 424/65 |
| 5,165,915 | 11/1992 | Takuho | 424/63 |
| 5,180,579 | 1/1993 | Birtwistle | 424/70 |
| 5,197,814 | 3/1993 | Lombardi | 401/78 |
| 5,198,210 | 3/1993 | Crithcley | 424/78.03 |
| 5,198,218 | 3/1993 | Kuznitz | 424/401 |
| 5,198,470 | 3/1993 | Zysman | 514/785 |
| 5,206,020 | 4/1993 | Critchley | 424/401 |
| 5,221,342 | 6/1993 | Minami | 106/461 |
| 5,225,186 | 7/1993 | Castrogiovanni | 424/64 |
| 5,236,710 | 8/1993 | Guerrero | 424/401 |
| 5,250,291 | 10/1993 | Park | 424/66 |
| 5,254,109 | 10/1993 | Smith | 604/289 |
| 5,266,321 | 11/1993 | Shukuzaki | 424/401 |
| 5,288,482 | 2/1994 | Kreysik | 424/64 |
| 5,292,530 | 3/1994 | McCrea | 424/66 |
| 5,300,284 | 4/1994 | Wiechers | 424/70 |
| 5,302,380 | 4/1994 | Castrogiovanni | 424/63 |
| 5,310,547 | 5/1994 | Dunphy | 424/64 |
| 5,318,775 | 6/1994 | Shore | 424/64 |
| 5,326,565 | 7/1994 | Critchley | 424/401 |
| 5,342,134 | 8/1994 | Lombardi | 401/78 |
| 5,362,494 | 11/1994 | Zysman | 424/401 |
| 5,385,730 | 1/1995 | Ichinohe | 424/78.02 |
| 5,393,526 | 2/1995 | Castro | 424/195.1 |
| 5,415,855 | 5/1995 | Critchley | 424/61 |

(List continued on next page.)

FOREIGN PATENT DOCUMENTS

| | | |
|---|---|---|
| 0008105 | 3/1982 | European Pat. Off. . |
| 0514067 | 11/1992 | European Pat. Off. . |
| 0508038 | 3/1995 | European Pat. Off. . |
| 0521647 | 11/1995 | European Pat. Off. . |
| 704200 | 4/1996 | European Pat. Off. . |
| 0723776 | 1/1997 | European Pat. Off. . |
| 60-248604 | 12/1985 | Japan . |
| 61-083110 | 4/1986 | Japan . |
| 61-236716 | 10/1986 | Japan . |
| 1168607 | 7/1989 | Japan . |
| 4149120 | 5/1992 | Japan . |
| 20850 | 3/1995 | Japan . |
| 8225432 | 9/1996 | Japan . |
| 9020620 | 1/1997 | Japan . |
| 9048709 | 2/1997 | Japan . |
| 9048710 | 2/1997 | Japan . |
| 09071510 | 3/1997 | Japan . |
| 1453266 | 10/1976 | United Kingdom . |
| 9407844 | 4/1994 | WIPO . |
| 9516429 | 12/1994 | WIPO . |
| 9511000 | 4/1995 | WIPO . |
| 9640044 | 12/1996 | WIPO . |

OTHER PUBLICATIONS

Active Organics, Actiglide Product Bulletin Apr. 1995.
Amino Acid Based Humectant, Ajinimoto Product Bulletin Nov. 1996.

*Primary Examiner*—Jyothsna Venkat
*Attorney, Agent, or Firm*—Julie Blackburn

[57] ABSTRACT

A pigmented cosmetic stick composition comprising, by weight of the total composition:

1–40% of a volatile nonaqueous solvent having a viscosity of 0.5 to 5 centipoise at 25° C., 20–80% of a first nonvolatile oil which is a $C_{12-22}$ fatty ester of citric acid, 1–35% of a second nonvolatile oil, 1–30% of a wax having a melting point of 30 to 135° C. which is an ethylene homopolymer or ethylene copolymer, 0.1–25% of particulate matter having a particle size of 0.5 to 200 microns; and wherein the total amount of nonvolatile oil present in the stick is greater than about 31% by weight of the total composition.

19 Claims, No Drawings

U.S. PATENT DOCUMENTS

| | | | |
|---|---|---|---|
| 5,429,816 | 7/1995 | Hofrichter | 424/66 |
| 5,444,096 | 8/1995 | McCrea | 514/770 |
| 5,466,457 | 11/1995 | Schneider | 424/401 |
| 5,484,816 | 1/1996 | Yanagida | 514/725 |
| 5,505,937 | 4/1996 | Castrogiovanni | 424/64 |
| 5,516,511 | 5/1996 | Motley | 424/65 |
| 5,519,063 | 5/1996 | Mondet | 514/772.4 |
| 5,532,147 | 7/1996 | Nilsson | 435/100 |
| 5,534,246 | 7/1996 | Herb | 424/66 |
| 5,538,718 | 7/1996 | Aul | 424/64 |
| 5,556,613 | 9/1996 | Arnaud | 424/64 |
| 5,616,746 | 4/1997 | Mahieu | 554/66 |
| 5,618,523 | 4/1997 | Zysman | 424/70.1 |
| 5,635,165 | 6/1997 | Panitch | 424/65 |
| 5,690,918 | 11/1997 | Jacks et al. | 424/401 |

MOISTURIZING COSMETIC STICK COMPOSITIONS

This is a continuation of copending application(s) Ser. No. 08/918,134, filed Aug. 27, 1997.

TECHNICAL FIELD

The invention is in the field of color cosmetic stick compositions such as lipstick, eyeshadow sticks, foundation sticks, and the like.

BACKGROUND OF THE INVENTION

Colored cosmetic stick compositions are most often anhydrous. They are formulated with hydrophobic ingredients and water is rarely present. It is very desireable to make lipsticks that are moisturizing, particularly for older women who suffer from dryness of the skin and lips. In addition, these moisturizing lipsticks should provide excellent color, shine, slip, and long lasting wear. Lipsticks with moisturizing properties generally contain high levels of nonvolatile oils. However, such lipsticks are generally not long wearing because the oils tend to form a superficial layer on the lips and rubs off very easily. Water is often thought to be the ultimate moisturizer. However, most unexpectedly, lipsticks which contain appreciable levels of water tend to be more drying to the lips than anhydrous lipsticks.

The object of the invention is to formulate long wearing colored cosmetic stick compositions which moisturize the skin and lips.

The object of the invention is to formulate long wearing colored cosmetic stick compositions which provide shiny finish and good slip on application.

Another object of the invention is to formulate colored cosmetic sticks that exhibit bright, true color, and provide a soothing, cooling sensation when applied to the lips, where the cooling is achieved without including ingredients such as menthol in the formula.

SUMMARY OF THE INVENTION

The invention is directed to pigmented cosmetic stick compositions comprising, by weight of the total composition:

1–40% of a volatile nonaqueous solvent having a viscosity of 0.5 to 5 centipoise at 25° C., 20–80% of a first nonvolatile oil which is a $C_{16-22}$ fatty ester of citric acid, 1–35% of a second nonvolatile oil, 1–30% of a wax having a melting point of 30 to 135° C. which is an ethylene homopolymer or ethylene copolymer, 0.1–25% of particulate matter having a particle size of 0.5 to 200 microns; and wherein the total amount of nonvolatile oil present in the stick is greater than about 31% by weight of the total composition.

DETAILED DESCRIPTION

The term "stick" refers to cosmetic compositions having a consistency such that they can be molded into the form of a stick—for instance by being heated until molten and then poured into a mold and cooled. Also included within the definition of "stick" are compositions of the invention that are capable of being formed into sticks, but are poured into pans or other types of cake or cream forms to deliver certain consumer benefits. For example, an eyeshadow composition in accordance with the invention may be molded in the stick form, but it may be desired to pour it into a pan because this container is more desireable from a consumer standpoint.

VOLATILE SOLVENT

The colored cosmetic stick composition of the invention comprises 1–40%, preferably 5–35%, more preferably 10–30% of a volatile solvent. The term "volatile" means that the solvent has a vapor pressure of at least 2 mm. of mercury at 20° C. The viscosity of the volatile solvent is preferably 0.5 to 5 centipoise at 25° C. Such volatile solvents include volatile low viscosity silicone fluids such as cyclic silicones having the formula:

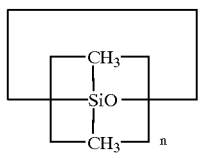

wherein n=3–7. Volatile linear polydimethylsiloxanes are also suitable and generally have from about 2 to 9 silicon atoms and are of the formula:

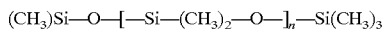

wherein n=0–7. These silicones are available from various sources including Dow Corning Corporation and General Electric. Dow Corning silicones are sold under the tradenames Dow Corning 244, 245, 344, 345, and 200 fluids. These fluids comprise octamethylcyclotetrasiloxane, decamethylcyclopentasiloxane, hexamethyldisiloxane, or mixtures thereof.

Also suitable as the volatile solvent component are straight or branched chain paraffinic hydrocarbons having 5–20 carbon atoms, more preferably 10–16 carbon atoms. Suitable hydrocarbons are pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70 to 190, more preferably 160–180, and a boiling point range of 30 to 320° C., preferably 60 to 260° C., and a viscosity of less than 20 centipoise at 25° C. Such paraffinic hydrocarbons are available from EXXON under the ISOPAR trademark as ISOPAR A, B, C, D, E, G, H, K, L, and M. Similar paraffinic hydrocarbons are also available from Shell Oil under the Shellsol trademark. in particular Shellsol 71; and from Phillips Petroleum under the tradename Solutrol 100, 130, and 220. In addition these paraffinic hydrocarbons may be purchased from Permethyl Corporation under the tradename Permethyl 99A or Permethyl R.

The volatile solvent may be a mixture of volatile silicone and paraffinic hydrocarbons, and if so, a ratio of 1:20 to 20:1 respectively is suggested.

THE FIRST NONVOLATILE OIL

The cosmetic stick compositions of the invention contain 20–80%, preferably 25–75%, more preferably 30–65% by weight of a first nonvolatile oil which is a $C_{12-22}$ fatty ester of citric acid. Preferably the fatty ester of citric acid is formed by the reaction of a $C_{12-22}$ fatty alcohol with citric acid. One, two, or three carboxylic acid groups of the citric acid may be esterified. The fatty acid ester of citric acid generally exhibits the following generic formula:

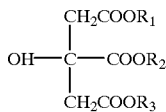

wherein $R_1$, $R_2$, and $R_3$ are each independently H, or a $C_{12-22}$, preferably a $C_{16-22}$ alkyl, more preferably a $C_{18-22}$ alkyl, with the proviso that $R_1$, $R_2$, and $R_3$ cannot all be hydrogen at the same time. Preferably, $R_1$, $R_2$, and $R_3$ are each a $C_{16-22}$ alkyl, preferably isostearyl and the compound is triisostearyl citrate.

THE SECOND NONVOLATILE OIL

The cosmetic stick compositions of the invention contain 1–30%, preferably 2–25%. more preferably 5–20% of a second nonvolatile oil. The term "nonvolatile" means that the oil has a vapor pressure of less than about 2 mm. of mercury at 20° C. A variety of nonvolatile oils are also suitable for use in the cosmetic sticks of the invention. The nonvolatile oils generally have a viscosity of greater than 10 centipoise at 25° C., and may range in viscosity up to 1,000,000 centipoise at 25° C., preferably being liquid to semi-solid at room temperature. Examples of nonvolatile oils suitable for use in the cosmetic sticks of the invention include esters of the formula RCO-OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate. octododecanol, and fatty alcohols such as oleyl alcohol, isocetyl alcohol, and the like.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil. linseed oil, mink oil, olive oil, palm oil, illipe butter, rapeseed oil, soybean oil. sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Straight or branched chain fatty alcohols having the formula R-OH, wherein R is a straight or branched chain saturated or unsaturated alkyl having 6–30 carbon atoms, are also suitable oils. Such fatty alcohols include cetyl alcohol, stearyl alcohol, cetearyl alcohol, and the like.

Also suitable as the oil are various lanolin derivatives such as acetylated lanolin, acetylated lanolin alcohol, and so on.

Nonvolatile silicones, both water soluble and water insoluble, are also suitable as the oil component. Such silicones preferably have a viscosity of 10 to 600,000 centistokes, preferably 20 to 100,000 centistokes at 25° C.

Suitable water insoluble nonvolatile silicones include amodimethicone, bisphenylhexamethicone, dimethicone, hexadecyl methicone, methicone, phenyl trimethicone, siimethicone, dimethylhydrogensiloxane, stearoxytrimethylsilane, vinyldimethicone, and mixtures thereof. Also suitable are water soluble silicones such as dimethicone copolyol, dimethiconol, and the like. Such silicones are available from Dow Corning as the 3225C formulation aid, Dow 190 and 193 fluids, or similar products marketed by Goldschmidt under the ABIL tradename.

Also suitable as the nonvolatile oil are various fluorinated oils such as fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

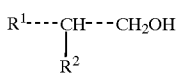

with a carboxylic acid having the general formula:

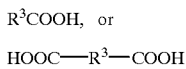

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil. Preferably, the guerbet ester is a fluoroguerbet ester which is formed by the reaction of a guerbet alcohol and carboxylic acid (as defined above), and a fluoroalcohol having the following general formula:

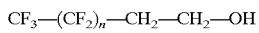

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech. Norcross Georgia as Developmental Ester L61125A, under the tradename Silube GMEF.

Preferably, the nonvolatile oil comprises naturally occuring glyceryl esters of fatty acids, or triglycerides, either alone or in combination with a water insoluble nonvolatile silicone such that the triglyceride is present at about 5–25% by weight of the total composition. If the water insoluble nonvolatile silicone is present, it is generally present from 0.5 to 8% by weight of the total composition. Preferably the triglyceride is lanolin oil and the water insoluble nonvolatile silicone is dimethicone.

WAX

The cosmetic stick compositions of the invention contain 1–30%, preferably 1–25%, more preferably 3–20% by weight of the total composition of a wax having a melting point of 30 to 135° C. which is an ethylene homopolymer or ethylene copolymer. The molecular weight of the ethylene homopolymer and/or copolymers used as the wax component may vary, so long as the melting point of the homo- or copolymer either alone or in combination is not greater than 135° C. Generally polyethylene waxes having a melting point range of 30 to 135° C. will have a molecular weight ranging from about 100 and 2,000. Preferably the ethylene copolymers are comprised of ethylene monomer units in either repetitive or randon sequence, in combination with monomer units of the following formula:

$$CH_2=CH—R_1$$

wherein $R_1$ is a $C_{1-30}$ straight or branched chain saturated or unsaturated alkyl, aryl, or aralkyl, preferably a $C_{1-10}$ straight or branched chain alkyl. Examples of ethylene homo- and copolymers which may be used in the invention are set forth in U.S. Pat. No. 5,556,613, which is hereby incorporated by reference.

PARTICULATE MATTER

The compositions of the invention comprise 0. 1–25%, preferably 0.5–20%, more preferably 1-18% by weight of the total composition of particulate matter having a particle size of 0.5 to 200, preferably 1–100 microns. The particulate matter may be colored or non-colored (for example white). Suitable powders include bismuth oxychloride, titanated mica, fumed silica, spherical silica, polymethylmethacrylate, micronized teflon, boron nitride, acrylate copolymers. aluminum silicate, aluminum starch octenylsuccinate, bentonite, calcium silicate, cellulose, chalk, corn starch, diatomaceous earth, fuller's earth, glyceryl starch, hectorite. hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide. trimagnesium phosphate, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

The particulate matter component also may comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines. chromium, chromium hydroxide colors, and mixtures thereof.

The composition may contain a mixture of both pigmented and non-pigmented powders. The percentage of pigments used in the powder component will depend on the type of cosmetic being formulated.

OTHER INGREDIENTS

The compositions of the invention may contain other ingredients which maximize the beneficial moisturizing effects of the composition.

Polymers

It may be desired to add 0.0001–15%, preferably 0.005–10%, more preferably 0.01 to 5% by weight of other polymers which provide enhanced benefits such as shine, texture, feel, and the like to the film. Examples of suitable copolymers are set forth in U.S. Ser. Nos. 918,136; 918,130: and 917,898; filed Aug. 27. 1997, all entitled "Cosmetic Compositions", filed on the same day as this application, by inventors Waifong Liew Anton, Milan Bohuslav Bednarek, Joseph Frank Calello, Natividad Jose, Anjali Abhimanyu Patil, Julio Gans Russ, Robert Walter Sandewicz, and Ann Marshall Urenick, which applications are hereby incorporated by reference. Preferably the polymers are uncrosslinked synthetic polymers comprising a first repeat unit selected from group consisting of methacrylate ester monomers which, if polymerized, would yield a polymer having a glass transition temperature ranging from about –10 to 75° C.; and a second repeat unit selected from the group consisting of methacrylate ester monomers which, if polymerized, would yield a polymer having a glass transition temperature ranging from about 76 to 120° C.; wherein the synthetic polymer has a glass transition temperature of 20 to 105° C. Preferably, the first repeat unit comprises at least one methacrylate ester monomer which, if polymerized to a molecular weight average of about 20,000. would yield a polymer having a glass transition temperature in the range of about –10 to 75° C. Preferably the second repeat unit comprises at least one methacrylate ester monomer which, if polymerized to a molecular weight average of about 20,000 would yield a polymer having a glass transition temperature in the range of about 76 to 120° C. The final polymer may contain, in addition to the first and second repeat units, other monomeric units such as styrene. ethylenically unsaturated monomer units such as ethylene, propylene. butylene, etc., vinyl monomers such as vinyl chloride, styrene, silicon repeat units, and so on, provided that the final polymer has at least one first repeat unit having a glass transition temperature ranging from about –10 to 75° C., and at least one second repeat unit having a glass transition temperature ranging from about 76 to 120° C., wherein the final polymer has a glass transition temperature ranging from about 20 to 105° C.

A variety of methacrylate ester monomers are suitable for use as first repeat unit. Preferably, the methacrylate ester monomers are aliphatic esters of methacrylic acid, such as is obtained with the esterification of methacrylic acid with an aliphatic alcohol of 2 to 30, preferably 2 to 20, more preferably 2 to 8 carbon atoms. If desired the aliphatic alcohol may have one or more hydroxy groups. Preferably the first repeat unit comprises isobuty Imethacry late, n-buty lmethacrylate. hydroxyethylmethacrylate, ethylhexylmethacry late, and the like.

A variety of monomers are suitable for use as the second repeat unit. Preferably the second repeat unit is methacrylic acid esterified with an aliphatic alcohol of 1 to 30 carbon atoms or an unsaturated camphene ring. More preferably the second ethylenically unsaturated monomer is isobornyl methacrylate or methylmethacrylate.

Preferably, the first and second repeat units each independently have the following general formula:

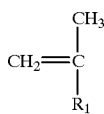

wherein $R_1$ is COOM wherein M is a substituted or unsubstituted $C_{1-30}$ straight or branched chain alkyl where the substitutents are halogen or alkoxy; pyrrolidone; or a substituted or unsubstituted aromatic cyclic, alicylic, or bicyclic ring where the substitutents are $C_{1-30}$ straight or branched chain alkyl or halogen.

Preferably, in first repeat unit $R_1$ is COOM where M is $C_{1-30}$ alkyl, more preferably M is a $C_{1-10}$ alkyl, more preferably M is a $C_{1-5}$ alkyl, and most preferably M is a $C_4$ branched chain alkyl, or isobutyl.

Preferably, in the second repeat unit, $R_1$ is COOM where M is H or $C_{1-30}$ alkyl or a alicyclic or bicyclic ring, more preferably $R_1$ is COOM where M is a $C_{1-5}$ alkyl or an alicyclic ring, and most preferably $R_1$ is COOM where M is $CH_3$ or an alicyclic ring which is isobornyl.

Particularly preferred is a copolymer of isobutylmethacrylate and isobornyl methacrylate comprising about 40–60% by weight of each monomer unit, wherein the polymer has a glass transition temperature of about 20 to 105° C. and a molecular weight average of about 5,000 to 300,000, preferably 5,000 to 50,000. Most preferably, the preferred polymer of the invention is a copolymer comprising a 50/50 ratio of isobutyl methacrylate and isobornyl methacrylate, which has a glass transition temperature of about 77° C., and a molecular weight of about 5,000 to 50,000.

Also suitable are acrylates copolymers like those disclosed in U.S. Pat. No. 4.996,044, which is hereby incorporated by reference. Such acrylates copolymers are generally powder materials having a molecular weight of 100,000 to 1,000,000, and comprise copolymers of acrylic acid or acrylic acid ester moieties. Particularly preferred is a copolymer known by the CTFA name "acrylates copolymer" which is defined as a polymer of two or more monomers consisting of acrylic acid, methacrylic acid, or their simple esters.

Preferably the compositions of the invention contain one or more polymers, in particular a combination of a acrylates copolymer and the copolymer mentioned above, having a glass transition temperature of about 20 to 105° C.

Preservatives

The composition may contain 0.0001–8%, preferably 0.001–6%, more preferably 0.005–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, calcium benzoate, calcium propionate, captan, chlorhexidine diacetate, chlorhexidine digluconate, chlorhexidine dihydrochloride, chloroacetamide, chlorobutanol, p-chlorom-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate. DMDM Hydantoin, and all of those disclosed on pages 570 to 571 of the CTFA Cosmetic Ingredient Handbook, Second Edition, 1992, which is hereby incorporated by reference.

Vitamins and Antioxidants

The compositions of the invention may contain vitamins and/or coenzymes, as well as antioxidants. If so, 0.001–10%, preferably 0.01–8%, more preferably 0.05–5% by weight of the total composition are suggested. Suitable vitamins include the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D, C, and K, as well as derivatives thereof are suitable. Particularly preferred are derivatives of vitamin C such as magnesium ascorbyl phosphate.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

Ceramides

May be desireable to include sphingolipids such as natural and synthetic ceramides in the compositions of the invention. If so, 0.0001–3%, preferably 0.0005–2% more preferably 0.001–1% by weight of the total composition is suggested. Particularly preferred are synthetic ceramides like those taught in PCT WO 94/07844, entitled "Hydroxy Alkyl Amides of Dicarboxylic Acids and Their Use in Cosmetic Compositions". Such pseudoceramides have the following general formula:

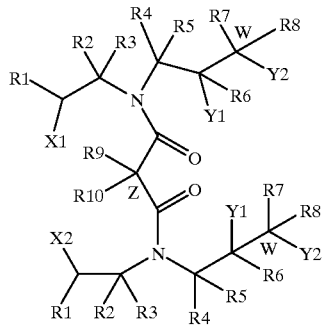

wherein R1 is a hydrocarbon group; R2-R8 are each independently H or CH3; R9 and R10 are each independently H or hydrocarbon group of up to 24 carbon atoms; X1 and X2 are each independently H or OH; Y1 and Y2 are H or OH, at least one of Y1 and Y2 being OH; wherein the C atom Z, with associated R9 and R10 can be absent; and the C atoms W, with associated R7 and Y2 can be absent, is disclosed. Particularly preferred is bishydroxyethyl biscetyl malonamide which is sold by Quest International under the tradename Questamide H.

Plant Extracts

It may also be desireable to add various types of plant extracts. If so, 0.0001–5%, preferably 0.001–4%, more preferably 0.01–2% is suggested. Suitable plant extracts include intact and hydrolyzed extensins such as those set forth in U.S. Pat. No. 5,443,855, which is hereby incorporated by reference. Also suitable are extracts of acacia extract. algae, alfalfa, aloe, gingko, bayberry, avocado, calendula, broom, apple, anise, birch, bitter orange, as well as those set forth on pages 493–494 of the CTFA Cosmetic Ingredient Handbook, Second Edition, 1992, which is hereby incorporated by reference. Particularly preferred gingko biloba extract.

Carbohydrates

It may be desireable to add one or more carbohydrates, which exert a humectant and emollient-type effect on the skin. If so, a range of 0.001–4%, preferably 0.005–3%, more preferably 0.01–2% by weight of the total composition is suggested. Suitable carbohydrates are mono-, di-, or polysaccharides, glycosaminoglycans, and derivatives thereof. Preferred are glucose, sucrose, and derivatives thereof such as methyl glucose dioleate, methyl glucose sesquiisostearate, methyl glucose sesquioleate, sucrose cocoate, sucrose palmitate, sucrose stearate, sucrose tribehenate, sucrose tristearate, and those disclosed on page 497 of the CTFA Cosmetic Ingredient Handbook, Second Edition, 1992, which is hereby incorporated by reference. Preferred is methyl glucose sesquiisostearate and hydrolyzed glycosaminoglycans.

Sterols

It may be desireable to include one or more sterols in the compositions of the invention. If so, about 0.0001–5%, preferably 0.0005–4%, more preferably 0.001–3% by weight of the total composition is suggested. Suitable sterols are animal or vegetable derived isocyclic compounds which exhibit a tetracyclic cyclopenteneophenanthrene skeleton as set forth below:

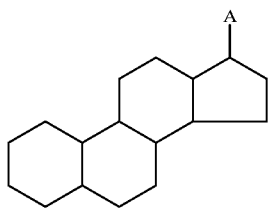

The above skeleton may contain hydroxyl or keto groups, some ring unsaturation, methyl groups, or aliphatic side chains at the A, or C-17, position. Examples of suitable sterols include C10-30 cholesterol/lanasterol, esters cholecalciferol, cholesterol, cholesteryl hydroxystearate, choleth-10, choleth-20, choleth-24, dihydrocholeth-1 5, tall oil sterol, soy sterol, lanolin alcohol, lanosterol, dihydrocholesterol, PEG soya sterol and the like. Preferred is $C_{10\text{-}30}$ cholesterol/lanasterol, which are cholesterol and lanasterol esterified with a $C_{1\text{-}30}$ fatty acid.

Humectants

It may also be desireable to include 0.0001–5%, preferably 0.0005–4%, more preferably 0.001–3% by weight of one or more materials that act as humectants; such as organic salts formed by the reaction of an organic base with either inorganic or organic acid, or by the reaction of an inorganic base with an organic acid. Examples of organic salts that provide a humectant effect are sodium PCA, sodium lactate, sodium stearoyl lactate, and the like. Preferred is sodium PCA.

Preferred is a composition containing one or more of the above ingredients either alone or in combination. Preferably, the ingredients are pre-formed as a complex, and added to the lipstick composition.

The invention will be further illustrated in connection with the following examples which are set forth for the purpose of illustration only.

EXAMPLE 1

| A cosmetic lipstick composition was made according to the following formula | |
|---|---|
| | w/w % |
| Synthetic wax | 8.50 |
| Paraffin wax | 2.00 |
| Triisostearyl citrate | 36.40 |
| Dimethicone | 1.40 |
| Cholesterol/lanasterol esters | 1.00 |
| Red iron oxides | 3.54 |
| D&C Red #7 Calcium Lake | 0.78 |
| FD&C Yellow #5 Aluminum Lake | 1.55 |
| Black iron oxides | 1.76 |
| Titanium dioxide | 2.37 |
| Lanolin oil | 20.30 |
| Moisturizing complex* | 0.25 |
| Phytosterol/octyldodecyl/lauryl glutamate | 0.05 |
| Cyclomethicone | 20.00 |
| Polymer solution*** | 0.10 |

***A solution containing about 90 parts by weight of a copolymer containing about equal parts by weight of isobutyl methacrylate and isobornyl methacrylate and about 10 parts by weight of isododecane.
*Moisturizing complex

| | w/w % |
|---|---|
| Bis-diglyceryl polyacyladipate | 15.00 |
| Methyl glucose sesquistearate | 27.00 |
| Hydrogenated polyisobutene | 23.70 |
| Sodium PCA | 2.00 |
| Gingko extract | 1.00 |
| Sodium lactate/sodium PCA/urea/hydrolyzed collagen/sodium phosphate | 1.00 |
| Methyl paraben | 0.30 |
| Propyl paraben | 0.10 |
| Isocetyl stearate | 11.90 |
| Sodium hylauronate/hydrolyzed glycosaminoglycans | 9.00 |
| Magnesium ascorbyl phosphate | 0.50 |
| Pseudoceramide (Questamide H) | 1.00 |
| Acrylates copolymer | 7.50 |

The lipstick composition was made by combining the synthetic wax, paraffin wax, triisostearyl citrate, dimethicone, and cholesteryl lanasterol with heat to cause the waxes to melt. The pigments, lanolin oil, moisturizing complex and phytosterol mixture was then added with stirring to mix the ingredients. They cyclomethicone and Dupont polymer were added last. The mixture was poured into molds and allowed to cool to room temperature.

While the invention has been described in connection with the preferred embodiment, it is not intended to limit the scope of the invention to the particular form set forth, but, on the contrary, it is intended to cover such alternatives, modifications and equivalents as may be included within the spirit and scope of the invention as defined by the appended claims.

We claim:

1. A pigmented cosmetic stick composition comprising, by weight of the total composition:
    1–40% of a volatile nonaqueous solvent having a viscosity of 0.5 to 5 centipoise at 25° C.,
    20–80% of a first nonvolatile oil which is a $C_{12\text{-}22}$ fatty ester of citric acid,
    1–35% of a second nonvolatile oil,
    1–30% of a wax having a melting point of 30 to 135° C. which is an ethylene homopolymer or ethylene copolymer;
    0.1–25% of particulate matter having a particle size of 0.5 to 200 microns wherein the particulate matter comprises a mixture of pigments and powders, 0.0001–5% plant extracts,
0.001–4% carbohydrates,
0.0001–5% sterols; and
0.0001–5% humectants;
wherein the total amount of nonvolatile oil present in the stick is greater than about 31% by weight of the total composition.

2. The composition of claim 1 wherein the volatile nonaqueous solvent is a volatile silicone.

3. The composition of claim 1 wherein the volatile silicone is selected from the group consisting of:
(a) a cyclic silicone having the formula:

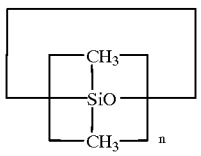

wherein n=3–7,
(b) a volatile linear polydimethylsiloxane having the formula:

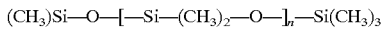

wherein n=0–7,
(c) straight or branched chain paraffinic hydrocarbons having 5–20 carbon atoms; and
(d) mixtures thereof.

4. The composition of claim 3 wherein the volatile solvent is a cyclic silicone.

5. The composition of claim 1 wherein the fatty ester of citric acid is the reaction product of a $C_{16-22}$ fatty alcohol with citric acid.

6. The composition of claim 5 wherein the fatty alcohol is stearyl alcohol.

7. The composition of claim 6 wherein the fatty ester of citric acid is triisostearyl citrate.

8. The composition of claim 1 wherein the second nonvolatile oil has a viscosity of about 10 to 1,000,000 centipoise at 25° C.

9. The composition of claim 8 wherein the second nonvolatile oil is selected from the group consisting of:
a) esters of the formula RCO—OR' wherein R and R' are each independently a $C_{1-25}$, straight or branched chain alkyl, alkenyl or alkoxycarbonylalkyl or alkylcarbonyloxyalkyl,
b) glyceryl esters of fatty acids,
c) nonvolatile hydrocarbons.
d) straight or branched chain fatty alcohols of the formula R—OH, wherein R is a straight or branched chain saturated or unsaturated alkyl having 6–30 carbon atoms,
e) nonvolatile silicones.
f) fluorinated oils.
g) guerbet esters, and
h) mixtures thereof.

10. The composition of claim 9 wherein the nonvolatile oil is selected from the group consisting of dimethicone, nonvolatile hydrocarbons, and esters of the formula RCO—OR' wherein R and R' are each independently a $C_{1-25}$, straight or branched chain alkyl, alkenyl or alkoxycarbonylalkyl or alkylcarbonyloxyalkyl.

11. The composition of claim 10 wherein the nonvolatile oil is dimethicone.

12. The composition of claim 1 wherein the wax contains ethylene monomer units in either repetitive or randon sequence.

13. The composition of claim 12 wherein comprises wax ethylene monomer units in either repetitive or randon sequence, in combination with monomer units of the following formula:

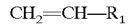

wherein $R_1$ is a $C_{1-30}$ straight or branched chain saturated or unsaturated alkyl, aryl, or aralkyl, straight or branched chain alkyl.

14. The composition of claim 1 wherein the pigments are organic pigments.

15. The composition of claim 1 wherein the plant extract is selected from the group consisting of extensin, acacia, algae, aloe, gingko, bayberry, avocado, calendula, broom, apple, anise, birch, bitter orange, and mixtures thereof.

16. The composition of claim 1 wherein the carbohydrate is a mono-, di-, or polysaccharide or glycosaminoglycan.

17. The composition of claim 1 wherein the carbohydrate is methyl glucose sesquiisostearate.

18. The composition of claim 1 wherein the sterol comprises a tetracyclic cyclopenfeneophenanthrene skeleton.

19. The composition of claim 1 wherein the humectant is an organic salt.

* * * * *